(12) United States Patent
Kemp et al.

(10) Patent No.: US 11,692,436 B2
(45) Date of Patent: Jul. 4, 2023

(54) MOLECULAR TRACERS AND MODIFIED PROPPANTS FOR MONITORING UNDERGROUND FLUID FLOWS

(71) Applicants: National Technology & Engineering Solutions of Sandia, LLC, Albuquerque, NM (US); UNM Rainforest Innovations, Albuquerque, NM (US)

(72) Inventors: Richard A. Kemp, Albuquerque, NM (US); Timothy J. Boyle, Albuquerque, NM (US)

(73) Assignees: National Technology & Engineering Solutions of Sandia, LLC, Albuquerque, NM (US); UNM Rainforest Innovations, Albuquerque, NM (US)

( * ) Notice: Subject to any disclaimer, the term of this patent is extended or adjusted under 35 U.S.C. 154(b) by 105 days.

(21) Appl. No.: 17/118,074

(22) Filed: Dec. 10, 2020

(65) Prior Publication Data

US 2021/0189866 A1 Jun. 24, 2021

Related U.S. Application Data

(60) Division of application No. 15/937,650, filed on Mar. 27, 2018, now Pat. No. 10,871,066, which is a (Continued)

(51) Int. Cl.
*E21B 47/11* (2012.01)
*E21B 43/267* (2006.01)
(Continued)

(52) U.S. Cl.
CPC ............ *E21B 47/11* (2020.05); *E21B 43/267* (2013.01); *C07D 487/22* (2013.01); *C09B 47/045* (2013.01)

(58) Field of Classification Search
None
See application file for complete search history.

(56) References Cited

U.S. PATENT DOCUMENTS 2,378,817 A 6/1945 Wrightsman et al.
2,675,335 A 4/1954 Rankin et al.
(Continued)

FOREIGN PATENT DOCUMENTS

GB 1401303 7/1975
GB 2528716 A 3/2016
WO 2014004815 A1 1/2014

OTHER PUBLICATIONS

Boyle, T. J. et al., "Synthesis and Characterization of Structurally Diverse Alkaline-Earth Salen Compounds for Subterranean Fluid Flow Tracking," Inorganic Chemistry (2018) 57:2402-2415.
(Continued)

*Primary Examiner* — Jeffrey D Washville
(74) *Attorney, Agent, or Firm* — Daniel J. Jenkins

(57) ABSTRACT

The present invention relates to modified proppants and methods of using the modified proppants that use metal ligand tracers to characterize subterranean fluid flow. The metal and ligands are best chosen to be a strongly-coordinating, chelating ligand with a functional group for the chosen flow environment.

8 Claims, 7 Drawing Sheets porphyrin-metal complex phthalocyanine-metal complex salen-metal complex

Related U.S. Application Data continuation-in-part of application No. 14/488,989, filed on Sep. 17, 2014, now Pat. No. 10,106,727.

(60) Provisional application No. 62/477,330, filed on Mar. 27, 2017.

(51) Int. Cl.
*C09B 47/04* (2006.01)
*C07D 487/22* (2006.01)

(56) References Cited

U.S. PATENT DOCUMENTS

| | | | |
|---|---|---|---|
| 3,002,091 | A | 9/1961 | Armstrong |
| 3,533,829 | A | 10/1970 | Quanquin |
| 3,993,131 | A | 11/1976 | Riedel |
| 4,179,429 | A | 12/1979 | Hanauye et al. |
| 4,427,068 | A | 1/1984 | Fitzgibbon |
| 4,440,866 | A | 4/1984 | Lunghofer et al. |
| 4,522,731 | A | 6/1985 | Lunghofer |
| 4,623,630 | A | 11/1986 | Fitzgibbon |
| 4,658,899 | A | 4/1987 | Fitzgibbon |
| 4,742,873 | A | 5/1988 | Craig, III |
| 4,873,145 | A | 10/1989 | Okada et al. |
| 4,879,181 | A | 11/1989 | Fitzgibbon |
| 4,888,240 | A | 12/1989 | Graham et al. |
| 5,218,038 | A | 6/1993 | Johnson et al. |
| 5,964,291 | A | 10/1999 | Bourne et al. |
| 6,279,656 | B1 | 8/2001 | Sinclair et al. |
| 7,036,591 | B2 | 5/2006 | Cannan et al. |
| 7,598,209 | B2 | 10/2009 | Kaufman et al. |
| 8,399,597 | B2 | 3/2013 | Pullichola et al. |
| 8,969,264 | B2 | 3/2015 | Jamison et al. |
| 2006/0177661 | A1 | 8/2006 | Smith et al. |
| 2008/0015103 | A1 | 1/2008 | Luscher et al. |
| 2008/0210421 | A1 | 9/2008 | Wilson et al. |
| 2009/0250216 | A1 | 10/2009 | Bicerano |
| 2010/0250207 | A1 | 9/2010 | Rodney |
| 2011/0177984 | A1 | 7/2011 | Wilson et al. |
| 2012/0181020 | A1 | 7/2012 | Barron et al. |
| 2012/0325473 | A1 | 12/2012 | Bicerano |
| 2013/0056204 | A1 | 3/2013 | McDaniel et al. |
| 2013/0126158 | A1 | 5/2013 | Gupta et al. |
| 2013/0138408 | A1 | 5/2013 | Lee et al. |
| 2014/0000891 | A1 | 1/2014 | Mahoney et al. |
| 2014/0187449 | A1 | 7/2014 | Khabashesku et al. |
| 2015/0292308 | A1* | 10/2015 | Conway .............. C09K 8/52 166/305.1 |
| 2016/0333260 | A1 | 11/2016 | Drake et al. |

OTHER PUBLICATIONS

Masters, K., Spray Drying Handbook, John Wiley and Sons, New York (1979).

Procedure 106-87-S of the American Foundry Society Mold and Core Test Handbook.

Ritter, S. K., "A New Way of Fracking," C&E N (2014) 92(19):31-33.

Hodgkins, K., http://www.digitaltrends.com/cool-tech/geothermal-power-dna-tracer/, Geothermal power's greatest hurdle may be solved by ball of DNA. Site last visited Jan. 15, 2017.

Dodge, J., http://source.colostate.edu/917/, Nanoparticles may aid oil recovery, frack fluid tracking, Aug. 14, 2014. Site last visited Jan. 15, 2017.

Kemp, R. A. et al., http://energy.gov/sites/prod/files/2015/06/f23/Track3_EGS_14_Sandia-CARBO-PIKernp.pdf "Tagged Nanoparticles for Fluid Flow Monitoring," Geothermal Technologies Office 2015 Peer Review, May 11, 2015, 14 pages. Site last visited Jan. 15, 2017.

http://www.glossary.oilfield.slb.com/en/Terms/p/proppant.aspx, Schlumberger Oilfield Glossary, 1 page. Site last visited Jan. 15, 2017.

Duenckel, R. J. et al., "Improvements in Downhole Chemical Delivery: Development of Multifunctional Proppants," SPE Hydraulic Fracturing Technology Conference, The Woodlands, Texas, Feb. 4-6, 2014; SPE 168605-MS, 10 pages.

Leasure, J. G., et al., "Effective Scale Prevention Using Chemically Infused Proppant—A Uinta Basin Case History," SPE International Symposium on Oilfield Chemistry, Apr. 13-15, The Woodlands, Texas, USA (2015) Society of Petroleum Engineers, SPE-173792-MS, 13 pages.

Dai, Z. et al., "Metalated porous porphyrin polymers as efficient heterogeneous catalysts for cycloaddition of epoxides with $CO_2$ under ambient conditions," Journal of Catalysis (2016) 338:202-209.

Meng, Q.-Y. et al., "Effect of Supercritical $CO_2$ on the Copolymerization Behavior of Cyclohexene Oxide/$CO_2$ and Copolymer Properties with DMC/Salen-Co(III) Catalyst System," Journal of Polymer Science Part A: Polymer Chemistry (2016) 54:2785-2793.

Rakhtshah, J. et al., "Synthesis, characterization and heterogeneous catalytic application of a nickel(II) Schiff base complex immobilized on MWCNTs for the Hantzsch four-component condensation," Journal of Coordination Chemistry (2017) 70(2):340-360.

Rezaeifard, A. et al., "Enhanced aqueous oxidation activity and durability of simple manganese(III) salen complex axially anchored to maghemite nanoparticles," RSC Adv. (2016) 6:64640-64650.

Sohn, C. et al., "Novel aluminum-BODIPY dyads: intriguing dual-emission via photoinduced energy transfer," Dalton Transactions (2016) 45:5825-5832.

Hernandez-Sanchez, B. A., et al., "Alkaline Earth Titanate ($A^E TiO_3$) Perovskite Nanoparticles Synthesized from Structurally Characterized Single-Source Alkoxides," Chem. Mater. (2007) 19:1459-1471.

Dolomanov, O. V. et al., "OLEX2: a complete structure solution, refinement and analysis program," Journal of Applied Crystallography (2009) 42:339-341.

Frisch, M. J.; et al. Gaussian 09, Revision A.02; Gaussian, Inc., Wallingford, CT, 2009, program for modeling.

Zhao, Y. et al., "The M06 suite of density functionals for main group thermochemistry, thermochemical kinetics, noncovalent interactions, excited states, and transition elements: two new functionals and systematic testing of four M06-class functionals and 12 other functionals," Theor. Chem. Account (2008) 120:215-241.

Dunning, Jr, "Gaussian basis sets for use in correlated molecular calculations. I. The atoms boron through neon and Hydrogen," J. Chem. Phys. (1989) 90(2):1007-1023.

Koput, J. et al., "Ab Initio Potential Energy Surface and Vibrational-Rotational Energy Levels of $X^2\Sigma^+ CaOH$," J. Phys. Chem. A (2002) 106:9595-9599.

Prascher, B. P. et al., "Gaussian basis sets for use in correlated molecular calculations. VII. Valence, core-valence, and scalar relativistic basis sets for Li, Be, Na, and Mg," Theor. Chem. Acc. (2011) 128:69-82.

Alberto, M. E. et al., "Photophysical properties of free and metallated meso-substituted tetrabenzotriazaporphyrin from density functional theory investigation," Dyes and Pigments (2015) 120:335-339.

Kim, D. Y. et al., "Operating mechanisms of electrolytes in magnesium ion batteries: chemical equilibrium, magnesium deposition, and electrolyte oxidation," Phys. Chem. Chem. Phys. (2014) 16:25789-25798.

Grosch, J. S. et al., "Molecular-Level Characterization of the Breathing Behavior of the Jungle-Gym-type DMOF-1 Metal-Organic Framework," J. Am. Chem. Soc. (2012) 134:4207-4215.

Terranova, Z. L. et al., "The effects of framework dynamics on the behavior of water adsorbed in the [Zn(I—L)(Cl)] and Co—MOF-74 metal-organic frameworks," Phys. Chem. Chem. Phys. (2016) 18:8196-8204.

Breneman, C. M. et al., "Determining Atom-Centered Monopoles from Molecular Electrostatic Potentials. The Need for High Sampling Density in Formamide Conformational Analysis," Journal of Computational Chemistry (1990) 11(3):361-373.

Mantina, M. et al., "Consistent van der Waals Radii for the Whole Main Group," J. Phys. Chem. A (2009) 113:5806-5812.

Sun, X.-Y. et al., "Luminescence properties of $Tb^{3+}$-activated silicate glass scintillator," Int. J. Mater. Res. (2011) 102:104-108.

(56) References Cited

OTHER PUBLICATIONS

Beale, J. P. et al., "The Crystal Structure of the Copper-Magnesium Complex with the Binucleating Schiff Base of Ethylenediamine with 3-Formylsalycylic Acid," Inorganica Chimica Acta (1979) 33:113-118.
Tao, R.-J. et al., "Synthesis and Crystal Structure of Dissymmetrical Double Schiff Base Cu(II) Homobinuclear and Cu(II)—Mg(II)—Cu(II) Heterotrinuclear Complexes," Chinese Journal of Chemistry (2006) 24:15591563.
Marsh, R. E., "Space groups P1 and Cc: how are they doing?" Acta Crystallographica Section B Structural Science (2009) 65:782-783.
Shan, W.-W. et al., "Redetermination of the crystal structure of aqua-methanol-bis[μ$_2$-N-(3-carboxylsalicylidene)-N'-(salicylaldehyde)-1,2-ethylenediamine-N,N',O,O,O',O']dicopper-(II)-magnesium(II)-methanol (1:1), [MgCu$_2$(H$_2$O)(CH$_3$OH)—(C$_{17}$H$_{13}$N$_2$O$_4$)$_2$]•CH$_3$OH,"Z. Kristallogr. NCS (2011) 226:207-209.
Sasmal, S. et al., "Tetrametallic [2x1+1x2], octametallic double-decker-triple-decker [5x1+3x1], hexametallic quadruple-decker and dimetallic-based one-dimensional complexes of copper(II) and s block metal ions derived from N,N'-ethylenebis(3-ethoxysalicylaldimine)," CrystEngComm (2010) 12:4131-4140.
Sarkar, S. et al., "Syntheses, crystal structures and supramolecular topologies of nickel(II)-s/p/d$^{10}$/NH$_4$$^+$complexes derived from a compartmental ligand," RSC Advances (2011) 1:640-650.
Mougel, V. et al., "Uranium and manganese assembled in a wheel-shaped nanoscale single-molecule magnet with high spin-reversal barrier," Nature Chemistry (2012) 4:1011-1017.
Constable, E. C. et al., "Host-guest chemistry of a chiral Schiff base copper(II) complex: can chiral information be transferred to the guest cation?" CrystEngComm (2010) 12:1764-1773.
Chiboub Fellah, F. Z. et al., "Varying the metal/metal ratio in related Cu—Ca complexes," Polyhedron (2007) 26:4209-4215.
Biswas, A. et al., "Syntheses, characterizations, and crystal structures of 3d-s/d$^{10}$ metal complexes derived from two compartmental Schiff base ligands," Journal of Coordination Chemistry (2013) 66(1):152-170.
Hazra, S. et al., "Syntheses and crystal structures of Cu$^{II}$Bi$^{III}$, Cu$^{II}$Ba$^{II}$Cu$^{II}$, [Cu$^{II}$Pb$^{II}$]$_2$ and cocrystallized (U$^{VI}$O$_2$)$_2$•4Cu$^{II}$ complexes: structural diversity of the coordination compounds derived from N,N'-ethylenebis(3-ethoxysalicylaldiimine)," CrystEngComm (2010) 12:470-477.
Escudero-Adán, E. C. et al., "Autocatalytic demetalation of a Zn(salphen) complex provoked by unprotected N-heterocycles," Dalton Transactions (2008) 734-737.
Carbonaro, L. et al., "Spectrophotometric Study of the Equilibria between Nickel(II) Schiff-Base Complexes and Alkaline Earth or Nickel(II) Cations in Acetonitrile Solution," Inorg. Chem. (1999) 38:5519-5525.
Van Veggel, F. C. J. M. et al., "Macrocyclic Trinucleating Ligands for the Cocomplexation of Two "Soft" (Cu$^{2+}$, Ni$^{2+}$, or Zn$^{2+}$) Metal Centers and One "Hard" (Ba$^{2+}$or Cs$^+$) Metal Center," J. Org. Chem. (1991) 56:225-235.
Hayami, S. et al., "Synthesis and structure of iron(III) complexes containing a quasi-crownether ring," Journal of Radioanalytical and Nuclear Chemistry (1999) 239(2):273-277.
Reglinski, J. et al., "Tetradentate Schiff base beryllium complexes," New J. Chem. (2015) 39:2437-2439.
Coleman, F. et al., "Solvent-dependent Switch of Magnesium Ions between Different Binding Sites in a Compartmental Schiff Base Ligand," Z. Anorg. Allg. Chem. (2013) 639(8-9):1584-1589.
Erxleben, A. et al., "Magnesium Versus Zinc Coordination to Multidentate Schiff Base Ligands," Eur. J. Inorg. Chem. (2001) 2001:3039-3046.
Sánchez, M. et al., "Salen-Type Compounds of Calcium and Strontium," Inorg. Chem. (2002) 41:5397-5402.
Westerhausen, M. et al., "Organocalcium Compounds with Catalytic Activity for the Ring-Opening Polymerization of Lactones," Eur. J. Inorg. Chem. (2003) 3432-3439.
Corazza, F. et al., "Five-co-ordinate Magnesium Complexes: Synthesis and Structure of Quadridentate Schiff-base Derivatives," J. Chem. Soc. Dalton Trans. (1988) 2341-2345.
Addison, A. W. et al., "Synthesis, Structure, and Spectroscopic Properties of Copper(II) Compounds containing Nitrogen-Sulphur Donor Ligands; the Crystal and Molecular Structure of Aqua[1,7-bis(N-methylbenzimidazol-2'-yl)-2,6-dithiaheptane]copper(II) Perchlorate," J. Chem. Soc. Dalton Trans. (1984) 1349-1356.
Mucha, F. et al., "Hexacoordinate Silicon-Azomethine Complexes: Synthesis, Characterization, and Properties," Monatshefte für Chemie (1999) 130:117-132.
Darensbourg, D. J. et al., "Cyclohexene Oxide/CO$_2$ Copolymerization Catalyzed by Chromium(III) Salen Complexes and N-Methylimidazole: Effects of Varying Salen Ligand Substituents and Relative Cocatalyst Loading," Inorg. Chem. (2004) 43:6024-6034.
Eltayeb, N. E. et al., "4,4',6,6'-Tetra-tert-butyl-2,2'-[1,2-phenylenebis-(nitrilomethylidyne)]diphenol acetone solvate," Acta Crystallographica Section E: Structure Reports Online (2008) 64:o576-o577.
Abd-Elzaher, M. M. et al., "Synthesis and Spectroscopic Characterization of Some Tetradentate Schiff Bases and Their Nickel, Copper and Zinc Complexes," Synth. React. Inorg. Met.-Org. Chem. (2000) 30(9):1805-1816.
Dimauro, E. F. et al., "Synthesis, Characterization, and Metal Complexes of a Salen Ligand Containing a Quinoline Base," Organometallics (2003) 22:850-855.
Narang, S. et al., "Synthesis of poly(propylene carbonate) from highly active, inexpensive achiral (Salph)Co(III)X as initiator and bis(triphenyl phosphine) iminium as co-initiator," J. Appl. Polym. Sci. (2016) 133:43099, 10 pages.
Shannon, R. D., "Revised Effective Ionic Radii and Systematic Studies of Interatomie Distances in Halides and Chaleogenides," Acta Cryst. (1976) A32:751-767.
Bahramian, B. et al., "Water-soluble manganese (III) salen complex as a mild and selective catalyst for oxidation of alcohols," Applied Catalysis A: General (2006) 315:52-57.
Chaube, V. D. et al., "Synthesis, characterization, and catalytic activity of Mn(III)- and Co(II)-salen complexes immobilized mesoporous alumina," Journal of Molecular Catalysis A: Chemical (2005) 241:79-87.
Troung, A., "How far underground are oil deposits?" Aug. 29, 2012. HowStuffWorks.com. http://science.howstuffworks.com/environmental/energy/underground-oil-deposits.htm. Site last visited Jan. 15, 2017, 2 pages.
SPE International PetroWiki: "Reservoir pressure and temperature" Jun. 3, 2015 http://petrowiki.org/Reservoir_pressure_and_temperature. Site last visited Jan. 15, 2017, 6 pages.
Kutasov, I., "Downhole temperature, pressure methods are accurate for drilling, completion, cement design," Sep. 16, 2002. Oil & Gas Journal, http://www.ogj.com/articles/print/volume-100/issue-38/drilling-production/downhole-temperature-pressure-methods-areaccurate-for-drilling-completion-cement-design.html. Site last visited: Jan. 15, 2017, 11 Pages.
Karstad, E. et al., "Temperature model provides information for well control" Sep. 14, 1998, http://www.ogj.com/articles/print/volume-96/issue-37/in-this-issue/drilling/temperature-model-providesinformation-for-well-control.html. Site last visited: Jan. 15, 2017, 17 pages.
Adamson, K. et al., "High-Pressure, High-Temperature Well Construction," Oilfield Review (1998) 36-49.
Conquest Version 5.39, Nov. 2017 update. Cambridge Crystallographic Data Centre: support@ccdc.cam.ac.uk or http://www.ccdc.cam.ac.uk/, database subscribed to search.
Greathouse, J. A. et al., "Computational Evaluation of Mg-Salen Compounds as Subsurface Fluid Tracers: Molecular Dynamics Simulations in Toluene-Water Mixtures and Clay Mineral Nanopores," Energy Fuels (2018) 32:4969-4978.
Boyle, T. J. et al., "Synthesis and characterization of thallium-salen derivatives for use as underground fluid flow tracers," Dalton Transactions (2018) 47:4162-4174.

\* cited by examiner

*porphyrin-metal complex*  *phthalocyanine-metal complex*  *salen-metal complex*

*Increased organic solubility based on bridge moiety and R-group*

| Chemical Name | Bridge, Modifier | Structure Schematic |
|---|---|---|
| 2,2'-((1E,1'E)-(ethane-1,2-diyl)bis(azaneylylidene))bis(methaneylylidene))diphenol | ethylene, H | |
| 6,6'-((1E,1'E)-(ethane-1,2-diyl)bis(azaneylylidene))bis(methaneylylidene))bis(2,4-di-*tert*-butylphenol) | ethylene, C(CH$_3$)$_3$ | |
| 6,6'-((1E,1'E)-(ethane-1,2-diyl)bis(azaneylylidene))bis(methaneylylidene))bis(2,4-dibromophenol) | ethylene, Br | |
| 6,6'-((1E,1'E)-(ethane-1,2-diyl)bis(azaneylylidene))bis(methaneylylidene))bis(2,4-dinitrophenol) | ethylene, NO$_2$ | |

FIGURE 4A

| | | |
|---|---|---|
| 2,2'-((1E,1'E)-(ethane-1,2-diylbis(azaneylylidene))bis(methaneylylidene))bis(4-((triphenyl-λ⁴-phosphaneyl)methyl)phenol), chloride salt | ethylene<br><br>[P(C₆H₅)₃][Cl] | 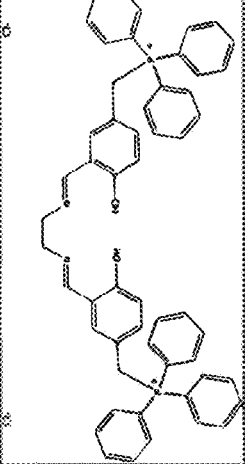 |
| 2,2'-((1E,1'E)-(1,2-phenylenebis(azaneylylidene))bis(methaneylylidene))diphenol | phenylene,<br><br>H | 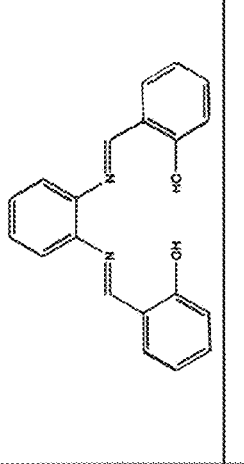 |
| 6,6'-((1E,1'E)-(1,2-phenylenebis(azaneylylidene))bis(methaneylylidene))bis(2,4-di-*tert*-butylphenol) | phenylene,<br><br>C(CH₃)₃ | 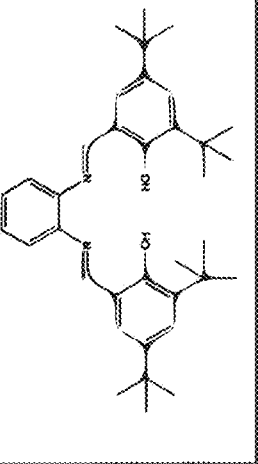 |
| 6,6'-((1E,1'E)-(1,2-phenylenebis(azaneylylidene))bis(methaneylylidene))bis(2,4-dibromophenol) | phenylene,<br><br>Br | 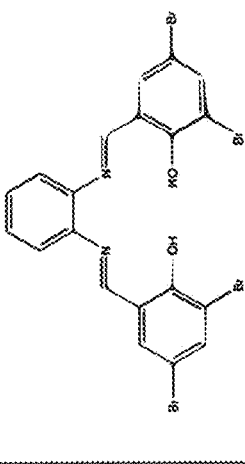 |

FIGURE 4B

| 6,6'-((1E,1'E)-(1,2-phenylenebis(azaneylylidene))bis(methaneylylidene))bis(2,4-dinitrophenol) | phenylene, NO₂ | |
|---|---|---|
| 2,2'-((1E,1'E)-(1,2-phenylenebis(azaneylylidene))bis(methaneylylidene))bis(4-(((triphenyl-λ⁴-phosphaney)methyl)phenol), chloride salt | Phenylene [P(C₆H₅)₃][Cl] | |

FIGURE 4C

| Chemical Name | Structure Schematic | Single Crystal structure plot |
|---|---|---|
| (pyridine)₂magnesium (k4-{O,N,N',O'}6,6'-{(1E,1'E)-(ethane-1,2-diylbis(azaneylylidene))bis(methaneylylidene)}bis(2,4-di-tert-butylphenoxide) Or [Mg(salo-Bu^t)(py)₂] |  |  |
| (pyridine)₂magnesium(k4-{O,N,N',O'}6,6'-{(1E,1'E)-(1,2-phenylenebis(azaneylylidene))bis(methaneylylidene)}bis(2,4-di-tert-butylphenoxide) Or [Mg(saloPh-Bu^t)(py)₂] |  |  |

MOLECULAR TRACERS AND MODIFIED PROPPANTS FOR MONITORING UNDERGROUND FLUID FLOWS

CROSS-REFERENCE TO RELATED APPLICATIONS

This application is a divisional of U.S. patent application Ser. No. 15/937,650, entitled "MOLECULAR TRACERS AND MODIFIED PROPPANTS FOR MONITORING UNDERGROUND FLUID FLOWS," filed on Mar. 27, 2018, which claims priority to U.S. Provisional Patent Application Ser. No. 62/477,330, entitled "SYSTEMS, METHODS AND PROPANTS FOR MONITORING UNDERGROUND FLUID FLOWS," by Richard A. Kemp, filed Mar. 27, 2017, and is a Continuation-in-Part of U.S. patent application Ser. No. 14/488,989, entitled "PROPPANT COMPOSITIONS AND METHODS OF USE," by Cannan et al., filed Sep. 17, 2014, the disclosures of which are incorporated herein by reference in their entireties.

STATEMENT OF GOVERNMENT INTEREST

The United States Government has rights in this invention pursuant to Contract No. DE-AC04-94AL85000 between the United States Department of Energy and Sandia Corporation, and pursuant to Contract No. DE-NA0003525 between the United State Department of Energy and National Technology & Engineering Solutions of Sandia, LLC, for the operation of the Sandia National Laboratories.

FIELD

The present disclosure is generally directed to monitoring underground fluid flows and more particularly to molecular metal ligand complex tracers.

BACKGROUND

Subterranean geothermal and shale-oil wells reside several kilometers below the surface of the earth. Currently, few viable fluid flow tracking methods exist that can accurately monitor and examine long-term fluid flows. When wells are opened, there are several paths of fluid-flow which need to be monitored. Accurately monitoring and determining the fluid flow of deep underground reservoirs (water or oil) is imperative to maximize the energy recovery from these wells.

The ability to actively track fluid flows to produce a 3D "model" of the reservoir has long been sought to improve the efficiencies in recovering products or energy from geothermal or hydrocarbon systems. Additionally, the ability to monitor these flows for extended periods of time—months to a year—is highly desired by industrial energy producers. One approach to develop this critical advanced monitoring technology of a hydraulically fractured, deep, hydrocarbon or hydrothermal reservoirs is to employ proppants capable of carrying tags or tracers that can be released over time. If certain readily identifiable tracers could be infused into and/or attached to proppants and controllably released, the proppants could be introduced at pre-determined locations in the reservoir, and the detection above-ground of the tracers at the well-head by some analytical technique would provide information that is both qualitative (which zone/sub-zone of the fractured well is producing) and quantitative (how much flow is being produced at each individual zone/sub-zone).

Known tracers include radioactive tracers, DNA fragments, and nanoparticles. As the reservoir fluids flow over, through and around the proppants, the tracers will be eluted into the "produced" fluids and transported to the well-head. For these tracers to be industrially valuable, they must be easily identified, inert from adhesion to the underground rock formations, and distinguished using standard/mobile analytical tools.

Prior art tracers have significant limitations: radioactive materials are not always considered environmentally friendly and do not yield the desired long-term fluid flow information, DNA fragments tend to degrade at the high temperatures and pressures encountered in these underground systems, and nanoparticles have been found to bind to subsurface strata and/or demonstrate poor stability.

What is needed is a new class of tracers that do not suffer from the drawbacks of existing tracers.

BRIEF DESCRIPTION OF THE DRAWINGS

FIG. 4A shows a listing of exemplary multidentate ligands according to an embodiment of the invention FIG. 4B is a continuation of FIG. 4A FIG. 4C is a continuation of FIG. 4A and 4B.

SUMMARY OF THE DISCLOSURE

In an embodiment, metal ligand (M-L) complexes are disclosed that are capable of being detected/identified by Fourier Transformed InfraRed (FTIR), Raman, and/or resonance Raman (rR) spectroscopy. In an embodiment, the M-L complexes include novel complexes consisting of transition metals, main group metals, and alkaline earth metals coordinated to multidentate ligands such as porphyrins, phthalocyanines or salens and their modified derivatives.

In another embodiment, proppants are disclosed that includes M-L complexes capable of being detected by FTIR, Raman, and/or rR spectroscopy.

In another embodiment, methods are disclosed that use M-L complexes capable of by FTIR, Raman, and/or rR spectroscopy detection for tracking subterranean fluid flows.

In another embodiment, methods are disclosed that use proppants with M-L complexes capable of by FTIR, Raman, and/or rR spectroscopy detection for tracking subterranean fluid flows.

In another embodiment, a modified proppant including a proppant and a M-L complex in contact with the proppant are disclosed.

In another embodiment, a composition having the formula [M(saloR'—R)(solv)$_x$], wherein M being Mg or Ca, R' being a bridge group selected as described herein, R being an attached group selected as described herein, solv being a solvent selected from a group as described herein, and x being between 1 and 4, is disclosed.

In another embodiment, a method is disclosed that includes introducing a modified proppant into a subterranean formation and collecting a fluid comprising the metal ligand complex from the subterranean formation. The modified proppant comprises a proppant and a metal ligand complex in contact with the proppant.

Other features and advantages of the present disclosure will be apparent from the following more detailed description of the preferred embodiment, taken in conjunction with the accompanying drawings which illustrate, by way of example, the principles of the disclosure.

BRIEF DESCRIPTION OF THE DRAWINGS

Wherever possible, the same reference numbers will be used throughout the drawings to represent the same parts.

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art.

Figure 1:
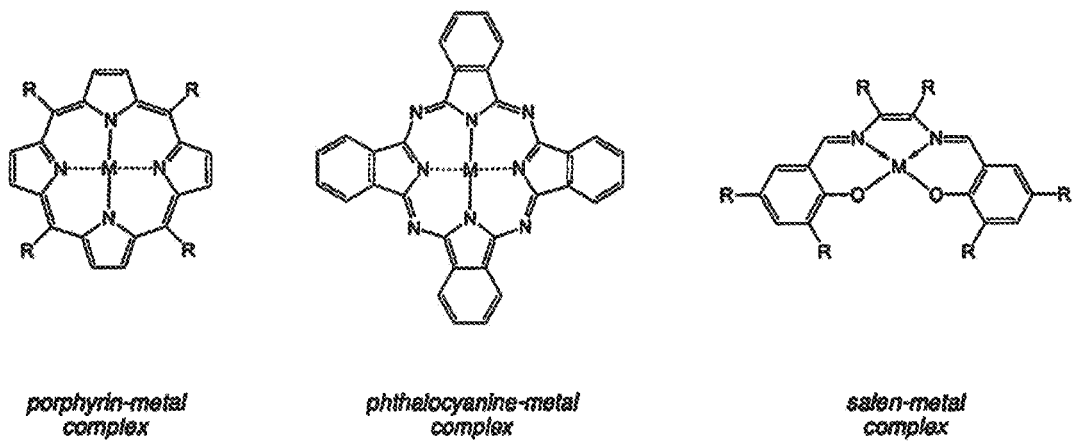
FIG. 1 shows various multidentate ligands according to an exemplary embodiment of the disclosure.

The present invention is directed to metal ligand (M-L) complexes capable of being detected by FTIR, Raman or the more sensitive resonance Raman (rR) spectroscopy for monitoring subterranean fluid flows. These M-L complexes in this use are referred to as tracers. The tracers include internal bridging groups and attached groups selected to tune the solubility of the tracer in organic or aqueous solutions or phases. The ligand coordinating species may be selected from a group including salens, porphyrins, phthalocyanines, and other multidentate ligands. The metal may be selected from a group including alkali earth, transition, lanthanides, actinides and main group metals including Mg, Ca, Sc, Ti, Zr, Hf, V, Fe, Co, Ni, Zn, Al, Ga, and In. FIG. 1 shows various multidentate ligands according to an embodiment of the disclosure.

The internal bridging group between the two halves of the ligand is selected to adjust the flexibility/solubility of the M-L complex within the desired solvent phase for example by allowing flexibility of the ligand to bind to the metal. In an embodiment, the bridging group may include (listed in general order from organic to aqueous phase solubility): ethylene, phenylene, alkyl- or aryl-substituted phenylene, naphthyl, cyclohexyl, etc.

In an embodiment, the attached functional group or attached group may include (listed in general order from organic to aqueous phase solubility) methyl, t-butyl, bromine, amino ($-NR_2$), nitrite ($-NO_2$). phosphonium ($R_4P^+$), derivatized sulfate ($RSO_3^-$), halides (X) groups. The $NR_2$ may be, but are not limited to alkyl, aryl, or silyl groups. In another embodiment, the attached groups may be, but are not limited to, hydrogen, methyl, propyl, t-butyl, phenyl, or similar organic groups. The $P^+$ groups may be, but are not limited to $Ph_3PCH_2-$, and may include similar functioning groups such as $Me_3PCH_2-$, $Pr_3PCH_2-$, $Ph_3AsCH_2-$, $Ph_3SbCH_2-$, and related compounds. The X modifiers may be, but are not limited to bromine, but may include other halides or pseudo-halides such as F, Cl, I, or $-CN$.

Figure 2:
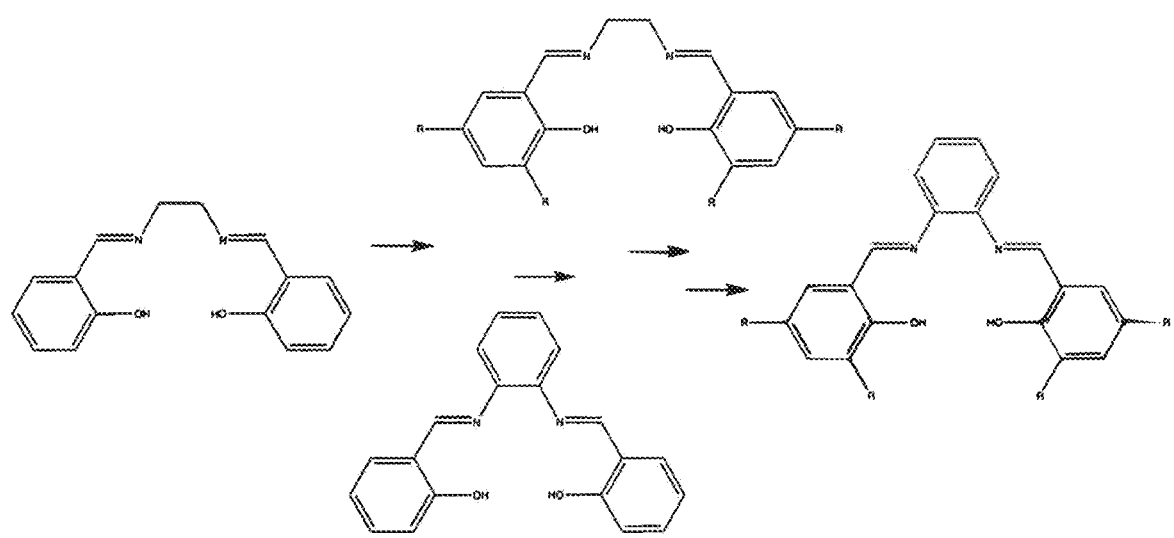
FIG. 2 shows general modifications for altering solubility to a parent salen ligand structure according to an exemplary embodiment of the disclosure.
Figure 3:
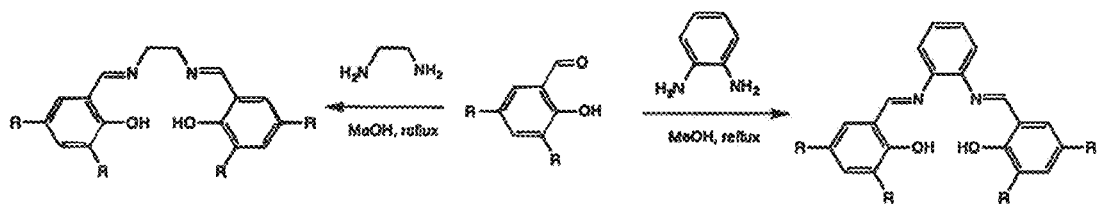
FIG. 3 shows a general synthesis for the preparation of ethylene, phenylene-bridged salen ligands according to an exemplary embodiment of the disclosure.

FIG. 2 shows a synthesis concept on altering the salen ligand peripheries according to an embodiment of the disclosure. It is understood that similar synthesis concepts apply to other multidentate ligands subject of this invention, all approaches being obvious to one with ordinary skill in the art of synthetic organic chemistry. As can be seen in FIG. 2, an organic ring bridging group was added to alter ligand flexibility and organic solubility. Attached groups (R) have been added to increase solubility for an organic or aqueous application. For example, $P^+$ groups provide greater aqueous solubility. In an embodiment, the solubility of the parent salen ligand in organic (oil) solvents can be improved by altering the bridging backbone or the aromatic rings through the addition of hydrophobic fragments, while the solubility in water can be increased by using hydrophilic fragments or ionic species to the backbone. FIG. 3 shows a general synthetic strategy for the preparation of ethylene, phenylene-bridged salen ligands according to an embodiment of the invention. FIGS. 4A, 4B and 4C are a listing of exemplary multidentate ligands according to an embodiment of the invention.

Note that most all of these complexes have additional coordinating solvent ligands attached to the metal in order to complete the coordination sphere of the metal. The formula may be written as [M(LR'—R)(solv)$_x$] with M being as discussed herein, L being the multidentate ligand, for example saloR'—R where the R' being a bridge group selected as described herein, R being an attached group selected as described herein, solv being a solvent selected from a group as described herein, and x being between 1 and 8. In an embodiment, x may be between 1 and 4. In another embodiment, x may be between 1 and 3. One of ordinary skill in the art would understand that the number of attached solvents would be determined by the metal.

It is critical that these additional solvent ligands on the M-L species are thermally stable and kinetically inert and do not leave the coordination sphere under conditions of temperature and pressure (mimicking underground conditions) as any molecular changes will undesirably affect the vibrational spectra and lead to ambiguity in identifying the released M-L complex. Several ligands have an important feature in that they contained aromatic groups as a key structural feature of the ligand, thus enhancing their sensitivity to vibrational techniques such as Raman as a distinguishing technique. In the following discussion the M-L ligands are discussed without reference to the attached solvent ligands, as these depend from the selection of the metal and ligand chemistry selected.

Figure 5:
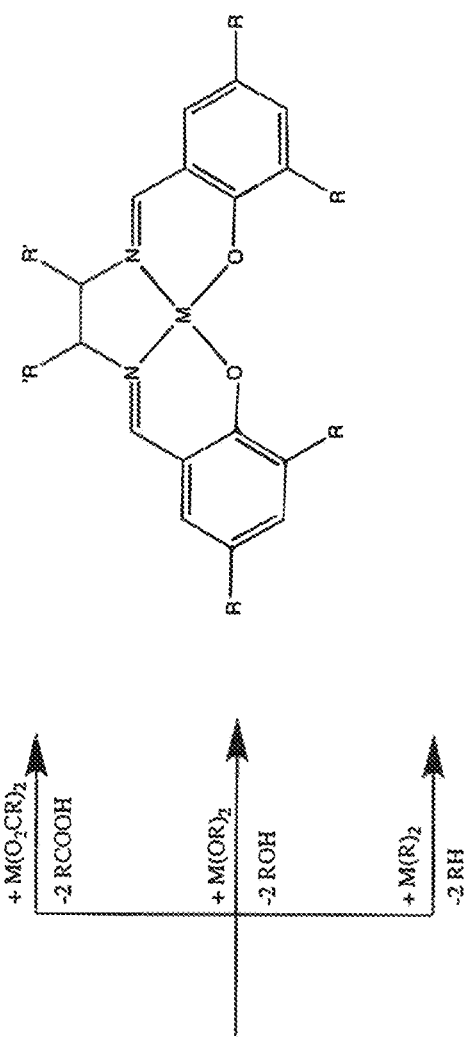
FIG. 5 shows a general synthetic procedure for the preparation of M-L complexes using salen ligands. A generic structure is used to represent all salen ligands.
Figure 5:
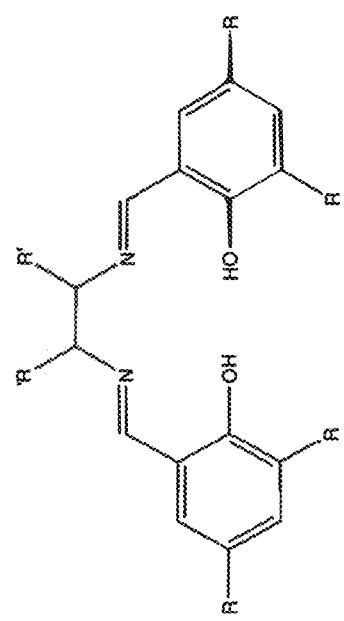

Next, the ligands were reacted with metal ions to prepare the final metal-ligand (M-L) complexes. These dianionic, chelating salen ligands, allow for classical methods of preparing M-L complexes to be utilized such as ion exchange, alcoholysis, metathesis, elimination of a smaller molecule such as an alcohol, and protonation/deprotonation of a metal alkyl. Some of these routes are shown in a general sense in FIG. 5.

Figure 6A:
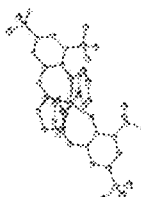
FIG. 6A shows exemplary novel M-L complexes according to an embodiment of the disclosure.
Figure 6A:
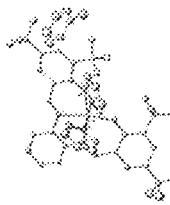
Figure 6A:
Figure 6A:
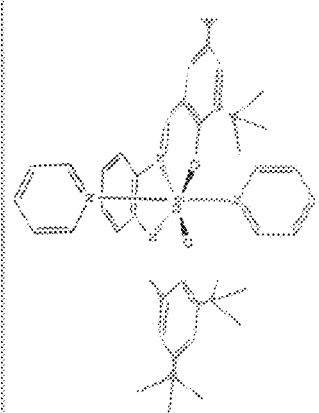
Figure 6B:
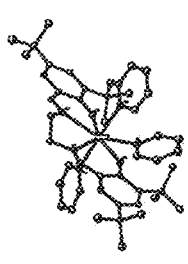
FIG. 6B is a continuation of FIG. 6A.

According to another embodiment of the disclosure, novel M-L complexes were synthesized. These novel M-saloR'—R complexes were formed through a tetra-chelation to the metals through the two O and two N atoms. These novel M-L complexes are [M(saloR'—R)(solv)$_x$] or [M(saloR'—R] without the solvent attachments (see discussion above regarding formula solvent representation), with M being Mg or Ca, R' being a bridge group selected as described herein, R being an attached group selected as described herein, solv being a solvent selected from a group as described herein, and x being between 1 and 3. In other embodiment, other synthesis as discussed above may be used. FIGS. 6A and 6B are a listing of exemplary novel multidentate ligands or novel metal-ligand complexes according to an embodiment of the disclosure.

The tracer should survive or remain stable under any suitable downhole conditions selected. According to an embodiment, some tracers disclosed may be survivable under temperatures up to about 150° C. In another embodiment, some disclosed tracers may be survivable under temperatures up to about 200° C.

The present disclosure is further directed to modified proppants containing the disclosed M-L complexes of this invention. The M-L complexes may be referred to as tracers. The term "proppant," as used herein, means material that includes one or more (e.g., tens, hundreds, thousands, millions, or more) of individual proppant particles, particulates or elements. The proppant may be porous or non-porous. Proppants include natural and synthesized materials. In an embodiment, proppants may be, but are not limited to lightweight ceramic proppant, intermediate strength proppant, high strength ceramic proppant, natural frac sand, porous ceramic proppant, glass beads and walnut hulls. The proppant may be or may include silica and/or alumina in any suitable amounts.

The term "apparent specific gravity", as used herein, is the weight per unit volume (grams per cubic centimeter) of the particulates, including the internal porosity. The apparent specific gravity values given herein were determined by the Archimedes method of liquid (water) displacement according to API RP60, a method which is well known to those of ordinary skill in the art. For purposes of this disclosure, methods of testing the characteristics of the proppant in terms of apparent specific gravity are the standard API tests that are routinely performed on proppant samples. The term "conductivity", as used herein, is defined as the product of the width of the created fracture and the permeability of the proppant that remains in the fracture. The term "high density proppant", as used herein, means a proppant having an apparent specific gravity of greater than 3.4 g/cm. The term "intermediate density proppant", as used herein, means a proppant having an apparent specific gravity of from about 3.1 to 3.4 g/cm. The term "internal interconnected porosity" as used herein, is defined as a percentage of the pore volume, or void volume space, over the total Volume of a porous ceramic particulate or porous ceramic proppant. The term "light weight proppant" as used herein, means a proppant having an apparent specific gravity of less than 3.0 g/cm. The term "degradable" as used herein, means the ability of a chemical or coating to react to dissolve or break down into smaller components under one or more downhole conditions. The term "infuse" as used herein, means to inject, attach, introduce, or otherwise include a material into a porous substrate, such as a porous ceramic. The term "ceramic" as used herein, means any non-metallic, inorganic solid material. The term "synthetic ceramic proppant", as used herein, means any man-made or synthetic ceramic particulate(s). The term "proppant" as used herein, means material that includes one or more (e.g., tens, hundreds, thousands, millions, or more) of individual proppant particles, particulates or elements. The term "tracer" as used herein, means a material capable of being distinguished from a material removed from the fractured subterranean formation.

According to certain exemplary embodiments of the present invention, a proppant particulate containing one or more tracers is disclosed. The one or more tracers can be disposed on, attached to, coated on, absorbed into, infused into, or otherwise combined with the proppant particulate to produce the proppant containing one or more tracers, also referred to as a proppant containing a tracer. The proppant can be or include a ceramic particulate. The tracer containing proppant particulate can be synthetic and/or naturally occurring. For example, the tracer containing proppant particulate can include sand, proppant, porous synthetic ceramic proppant, and non-porous synthetic ceramic proppant. Preferred are porous proppants capable of loading high weight percentage levels of tracers. The tracer containing proppant particulate can also be coated with a resin and/or epoxy material. In an embodiment, the coating can include or otherwise contain the tracer. The proppant containing tracer can also be uncoated; however, for longer operating lifetimes a coating is preferred.

Also. according to certain exemplary embodiments of the present invention, a proppant containing a tracer or modified proppant for use in hydraulic fracturing is disclosed. The modified proppant may be part of a proppant composition that includes proppant containing and not containing a tracer. In an embodiment, the proppant composition can include a non-porous proppant portion and a porous proppant portion, wherein at least a portion of the porous proppant contains the tracer. Furthermore, according to certain embodiments of the present invention, the permeability and conductivity of the composite proppant composition is at least equal to the permeability and conductivity of the nonporous proppant part alone.

The tracer is contained by the proppant by one or more mechanisms, including adsorption, adhesion and coating. In an embodiment, the tracer is infused into the pores of a proppant. In an embodiment, the tracer is deposited onto the surface of the proppant. In an embodiment, the surface may be an external surface and/or an internal surface such as a pore surface. In an embodiment, the tracer may be solubilized in an organic or aqueous solvent before infusing, impregnating or coating upon the proppant. In an embodiment, the organic solvent may be hexanes, toluene, tetrahydrofuran, pyridine, chloroform, etc. In another embodiment, the aqueous solvent may be water.

The proppant may have any suitable shape. The proppant particulates can be substantially round, cylindrical, square, rectangular, elliptical, oval, egg-shaped, or pill-shaped. In an embodiment, the proppant can be substantially round and spherical. The proppant particulates can be substantially round, cylindrical, square, rectangular, elliptical, oval, egg-shaped, or pill-shaped. For example, the proppant particulates can be substantially round and spherical.

The porous ceramic proppant has an internal porosity, or percent (%) porosity. The internal porosity of the porous ceramic proppant can be infused with the tracer so that the porous ceramic proppant acts as a carrier for the tracer in a hydraulic fracturing operation. By tailoring the type of porous ceramic proppant used as a carrier, any potential impact to proppant conductivity by using the porous ceramic proppant can be avoided.

The proppant has any suitable size. For example, the proppant particulates can have a mesh size of at least about 6 mesh, at least about 10 mesh, at least about 16 mesh, at least about 20 mesh, at least about 25 mesh, at least about 30 mesh, at least about 35 mesh, or at least about 40 mesh. According to several exemplary embodiments, the proppant particulates have a mesh size from about 4 mesh, about 6 mesh, about 10 mesh, about 16 mesh, or about 20 mesh to about 25 mesh, about 30 mesh, about 35 mesh, about 40 mesh, about 45 mesh, about 50 mesh, about 70 mesh, or about 100 mesh.

According to several exemplary embodiments, the proppant may have an apparent specific gravity, size, porosity, pore size, internal connected porosity, permeability and conductivity of proppant as disclosed in U.S. Patent Publication Number 2016/0075937, hereby incorporated by reference in its entirety.

The proppant infused, impregnated or coated with the tracer can then be sealed. In an embodiment, sealing may be achieved by coating the proppant containing tracer with a polymer, epoxy, or other suitable coating material capable of retarding the rapid elution of tracer molecules from the proppant under subterranean conditions. According to several exemplary embodiments, the coating material may include coating materials as disclosed in U.S. Patent Publication Number 2016/0075937, hereby incorporated by reference in its entirety.

It is desired that for most efficient use of the tracer that the tracer not elute from the proppant for an extended period of time underground, and the coating material extends the useful life by slowing the release of the tracer over a many month period. In such a manner, the time of release of the tracer can be calculated and extended to a desired, predetermined time. For example, the coating or sealing can inhibit the elution of the tracer to allow for elution for up to twelve months. In another embodiment, the coating or sealing can inhibit the elution of the tracer to allow for elution for up to nine months. In another embodiment, the coating or sealing can inhibit the elution of the tracer to allow for elution for up to three months. In yet other embodiments the coating or sealing can be engineered to inhibit the elution of the tracer to allow for elution up to a predetermined period of time.

According to several exemplary embodiments, at least a portion of the proppant particulates of the proppant are coated with a polymer or resin material. According to several exemplary embodiments, at least about 50%, at least about 75%, at least about 85%, at least about 90%, at least about 95%, or least about 99%, or all of the surface of the proppant particulates in the proppant composition are coated with the resin material. According to several exemplary embodiments, the resin material is present on the resin coated proppant particulates in any suitable amount. According to several exemplary embodiments, the resin material includes any suitable resin. For example, the resin material can include a phenolic resin, such as a phenol formaldehyde resin. According to several exemplary embodiments of the present invention, the resin coating applied to the proppant particulates is an epoxy resin. The coating material may be as disclosed in U.S. Patent Publication Number 2016/0075937, hereby incorporated by reference in its entirety.

Example of Depositing a Tracer into a Porous Proppant

After preparation of the various M-L complexes, the next step in the process to make the loaded proppant was to infuse (or impregnate) the M-L complex into a commercial, porous proppant. The ceramic porous proppant had had approximately 0.11 cc/g of interconnected pore volume, and this volume was used to deposit the M-L complexes. In this example, it was desired to not include tracer onto the surface of the proppant. In order to prevent the M-L complex from depositing on the surface of the proppant, no more than 90% of the available pore volume was to be occupied by the M-L complex solution at any time. The desired weight loading target for the complex was between 2 and 6 wt. %. The experimental procedure for loading the proppant was as follows. To a pre-weighed vial, the desired amount of M-L complex was added to 10 mL of toluene to create as concentrated a solution as possible. A 10 g portion of porous proppant was weighed into a separate vial. For each loading, ~0.8 mL of M-L-toluene solution was added dropwise to the vial containing proppant, after each addition the vial was shaken to ensure the compound was taken-up by the porous proppant via capillary forces. After each addition, the excess toluene was removed via gentle heating in vacuo. This process was repeated as many times as needed until the desired total wt. % loading was achieved. Ultimately higher weight loadings of the M-L complex leads to longer useful lifetimes in a practical application such as hydraulic fracturing.

At this point, the porous proppant package consisted of the desired M-L complex deposited upon the pore walls of the ceramic proppant. The next step in preparing the package was to coat the proppant with an epoxy coating to help "time release" the M-L complex from the proppant during use.

Example of Magnesium (Mg) and Calcium (Ca) (Alkaline Earth) Salen-Derivatives Synthesis A family of magnesium and calcium salen-derivatives was synthesized and characterized for use as subterranean fluid flow monitors. For the Mg complexes, di-n-butyl magnesium ($[Mg(Bu'')_2]$) was reacted with N,N'-ethylene bis(salicylideneimine) ($H_2$-salen), N,N'-bis(salicylidene)-1,2-phenylenediamine ($H_2$-saloPh), N,N'-bis(3,5-di-t-butylsalicylidene)-ethylenediamine ($H_2$-salo-Bu$^t$), or N,N'-bis(3,5-di-t-butylsalicylidene)-1,2-phenylenediamine ($H_2$-saloPh-Bu) and the products were identified by single crystal X-ray diffraction as $[(\kappa^3$-(O,N,N'),$\mu$-(O')saloPh)($\mu$-(O),($\kappa^2$-(N,N'),$\mu$-(O')saloPh)$_2$($\mu$-(O), $\kappa^3$-(N,N',O')saloPh')Mg$_4$].2tol (1.2tol; saloPh'=an alkyl modified saloPh derivative generated in situ), $[(\kappa^4$-(O,N,N',O')saloPh)Mg(py)$_2$].py (2.py), $[([(\kappa^4$-(O,N,N',O')salo-But)Mg(py)$_2$] (3), $[(\kappa^4$-(O,N,N',O')saloPh-But)Mg(py)$_2$].tol (4.tol) (Note: 4.tol means that four toluene molecules are co-crystallized with the parent compound, and similar notations may be used further in this disclosure) and $[(\kappa^3$-(O,N,N'),$\mu$-(O')saloPh-But)Mg]$_2$ (5) where tol=toluene; py=pyridine. For the Ca species, a calcium amide was independently reacted with $H_2$-salo-But and $H_2$-saloPh-But to generate the crystallographically characterized compounds: $[((\kappa^4$-(O,N,N',O')salo-Bu$^t$)Ca(py)$_3$] (6) (Note: the parenthetical bold numbers are used to reference the molecular formula.), $[((\kappa^4$-(O,N,N',O')saloPh-But)Ca(py)$_3$].py (7.py) (Note: (7.py) means compound 7 was co-crystallized with a pyridine molecule in the unit cell, note that similar notation may be used with other compounds to represent similar meaning). The bulk powders of these compounds were further characterized by a number of analytical tools, where 2-7 were found to be distinguishable by FTIR and Raman spectroscopy. Structural properties obtained from quantum calculations of gas-phase analogs are in good agreement with the single crystal results.

The salen ligands ($H_2$-saloR'—R) studied include: (a) N,N'-ethylene bis(salicylideneimine) ($H_2$-salen), (b) N,N'-bis(salicylidene)-1,2-phenylenediamine ($H_2$-saloPh), (c) N,N'-bis(3,5-di-t-butylsalicylidene)-ethylenediamine ($H_2$-salo-Bu$^t$) and (d) N,N'-bis(3,5-di-t-butylsalicylidene)-1,2-phenylenediamine ($H_2$-saloPh-Bu). The products isolated from the reaction of di-n-butyl magnesium (Mg(Bu'')$_2$; eq 1) with the $H_2$-saloR'—R derivatives were crystallographically identified as: $[(\kappa^3$-(O,N,N'),$\mu$-(O')saloPh)($\mu$-(O),($\kappa^2$-(N,N'),$\mu$-(O')saloPh)$_2$($\mu$-(O),$\kappa^3$-(N,N',O')saloPh')Mg$_4$].2tol (1.2tol; saloPh'=an alkyl modified saloPh derivative generated in situ), $[(\kappa^4$-(O,N,N',O')saloPh)Mg(py)$_2$].py (2.py), $[(\kappa^4$-(O, N,N',O')salo-Bu$^t$)Mg(py)$_2$] (3), [(κ$^4$-(O,N,N',O')saloPh-Bu$^t$)Mg(py)$_2$].tol (4.tol), and [(κ$^3$-(O,N,N'),μ-(O')saloPh-Bu$^t$)Mg]$_2$ (5) where tol=toluene and py=pyridine. For the Ca species, calcium bis(trimethylsilyl)amide ([Ca(NR$_2$)$_2$]; eq 2) was independently reacted with H$_2$-salo-Bu$^t$ and H$_2$-saloPh-Bu$^t$ to generate the crystallographically characterized complexes [(κ$^4$-(O,N,N',O')salo-Bu$^t$)Ca(py)$_3$] (6) and [(κ$^4$-(O,N,N',O')saloPh-Bu$^t$)Ca(py)$_3$].py (7.py). These compounds were fully characterized using a variety of analytical techniques. Additionally, molecular modeling of the compounds was undertaken to analyze the impact that the different ligand modifications had on the degree of charge transfer between the metal ion and the organic components (sa-loR'—R moieties and py ligands). Electronic structure calculations were performed on individual compounds. The models were validated by comparing geometric properties with those obtained by single crystal diffraction experiments.

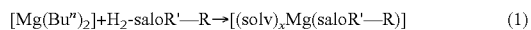

[Mg(Bu$''$)$_2$]+H$_2$-saloR'—R→[(solv)$_x$Mg(saloR'—R)]   (1)

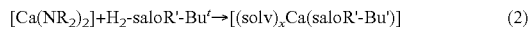

[Ca(NR$_2$)$_2$]+H$_2$-saloR'-Bu$^t$→[(solv)$_x$Ca(saloR'-Bu')]   (2)

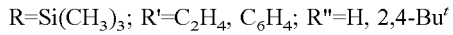

R=Si(CH$_3$)$_3$; R'=C$_2$H$_4$, C$_6$H$_4$; R''=H, 2,4-Bu$^t$

With this unique set of precursors available, preliminary investigations into the retention of the structure under simulated deep well conditions were investigated, including thermal/pressure, interaction with surfaces (SiO$_2$ columns), and elution data from the proppant.

Experimental

All compounds described below were handled with rigorous exclusion of air and water using standard Schlenk line and glovebox techniques unless otherwise discussed. Analytical data were collected on dried crystalline samples. All chemicals were used as received without further purification, including: methanol (anhydrous 99.8%) (MeOH), diethyl ether (anhydrous, 99.7%) (Et$_2$O), pyridine (py) (anhydrous, 99.8%), tetrahydrofuran (THF) (anhydrous, ≥99.9%), toluene (tol) (anhydrous, 99.8%), N,N'-bis(salicylidene)ethylenediamine (H$_2$-salen) (98%), N,N'-bis(salicylidene)-1,2-phenylenediamine (H$_2$-saloPh) (97%), calcium iodide (CaI$_2$), 1.0 M di-n-butyl magnesium solution ([Mg(Bu$''$)$_2$] in heptane), potassium bis(trimethylsilyl)amide (KNR$_2$), 3,5-di-tert-butyl-2-hydroxybenzaldehyde (99%), ethylene diamine (99%), pyridine-d$_5$ (py-d$_5$) (≥99.5 atom % D), and chloroform-d (CDCl$_3$; 99.8 atom % D). Ortho-phenylenediamine (98%). Calcium bis(trimethylsilyl)amide ([Ca(NR$_2$)$_2$]) was synthesized from the reaction of CaI$_2$ and 2 equivalents of KNR$_2$ in THF. Dried crystalline materials were used for all analytical analyses. A commercial porous proppant was provided by Carbo Ceramics, Inc., and is available from them under the product name 20/40 CarboUltraLite™.

FTIR data were collected on a Nicolet 6700 FTIR spectrometer using a KBr pellet press under a flowing atmosphere of nitrogen or with iD7 ATR accessory mounted with a monolithic diamond crystal. Elemental analyses were collected on a Perkin Elmer 2400 Series II CHNS/O Analyzer with samples prepared in an argon filled glovebox. Melting point data were collected using a Stanford Research Systems Optimelt MPA100. Raman spectra were obtained using a Thermo Scientific DXR Smart Raman instrument. All NMR samples were prepared under an argon atmosphere and flame sealed using crystalline material at as high a concentration as possible. Spectra were collected on a Bruker Avance 500 NMR spectrometer under standard experimental conditions: $^1$H analysis was performed with a 4-second recycle delay at 16 scans; $^{13}$C analysis was performed with a 10-sec recycle delay with a minimum of 64 scans. Alternatively, a Bruker Fourier 300 HD spectrometer or a Magritek Spinsolve Phosphorous benchtop spectrometer were also used. All spectra were referenced to the appropriate residual protonated species in the solvent. The Thermogravimetric Analysis (TGA)/Differential Scanning Calorimetry (DSC) analyses were obtained on a Mettler Toledo model TGA/DSC 1. All experiments were conducted under an argon atmosphere at a heating rate of 10° C. min$^{-1}$ from room temperature to 750° C. in an alumina crucible.

Ligand Synthesis.

H$_2$-salo-Bu$^t$. 3,5-di-tert-butyl salicylaldehyde (4.68 g, 20.0 mmol) and ethylene diamine (0.600 g, 9.98 mmol) were added to a 500 mL round bottom flask containing MeOH (~225 mL). After stirring at 65° C. for 17 h, the reaction was allowed to cool to room temperature. The resulting precipitate was isolated by filtration, rinsed with Et$_2$O (3×20 mL), and dried in an oven at 100° C. for 24 h affording an off white/light yellow powder. Yield 96.1% (4.73 g). FTIR (cm$^{-1}$; iD7 ATR): 3254 (w(br), —OH), 3051 (w), 2956 (s), 2867 (m), 1626 (s, C=N), 1594 (m), 1464 (s), 1438 (s), 1392 (m), 1360 (s), 1252 (m), 1172 (s), 1040 (s), 879 (s), 829 (s), 773 (s), 709 (s), 644 (s). $^1$H NMR (300 MHz, py-d$_5$) δ $^1$H NMR (500.1 MHz, CDCl$_3$): 13.64 (s, 2H, —OH), 8.40 (s, 2H, —CHN—), 7.36 (d, 2H, C$_6$H$_2$(C(CH$_3$)$_3$)$_2$), 7.08 (d, 2H, C$_6$H$_2$(C(CH$_3$)$_3$)$_2$), 3.94 (s, 4H, N(CH$_2$)$_2$N); 1.45 (s, 18H, C(CH$_3$)$_3$); 1.30 (s, 18H, C(CH$_3$)$_3$). Anal. Calc'd for C$_{32}$H$_{48}$N$_2$O$_2$ (MW=492.75): C, 78.00; H, 9.82; N, 5.69. Found: C, 78.43; H, 9.96; N, 5.57. MP 184-187° C.

H$_2$-saloPh-Bu$^t$. 3,5-di-tert-butyl salicylaldehyde (2.24 g, 9.56 mmol) and o-phenylenediamine (0.59 g, 5.46 mmol) were added to a 250 mL round bottom flask containing 75 mL of MeOH. After stirring at 65° C. for 17 h, the reaction was allowed to cool to room temperature. The resulting precipitate was isolated by filtration, rinsed with Et$_2$O (3×20 mL), and dried in an oven at 100° C. for 24 h. This afforded a light-yellow powder. Yield: 72.1% (1.95 g). FTIR (cm$^{-1}$; iD7 ATR): 3368 (w(br), —OH), 3056 (w), 2951 (s), 2905 (m), 2866 (m), 1805 (w), 1615 (s, C=N), 1570 (s), 1479 (m), 1438 (s), 1360 (s), 1251 (m), 1169 (s), 1104 (m), 973 (m), 877 (m), 820 (m), 755 (s), 643 (m). $^1$H NMR (43 MHz, CDCl$_3$): 13.52 (s, 2H, —OH), 8.66 (s, 2H, —CHN—), 7.18-7.41 (m, 4H, C$_6$H$_2$(C(CH$_3$)$_3$)$_2$), 1.45 (s, 18H, —C(CH$_3$)$_3$), 1.34 (s, 18H, —C(CH$_3$)$_3$). Anal. Calc'd for C$_{36}$H$_{48}$N$_2$O$_2$ (MW=540.79): C, 79.96; H, 8.95; N, 5.18. Found: C, 80.40; H, 8.68; N, 4.97. MP 194-197° C.

General Mg-salen reaction. In an inert atmosphere glove box, a pre-weighed sample of the desired H$_2$-saloR'—R was added to a stirring solution of [Mg(Bu$''$)$_2$] in toluene. After stirring for 12 h, py was added and the reaction stirred for at least an additional hour. This reaction was set aside until X-ray quality crystals grew.

[(κ$^4$-(O,N,N',O')saloPh)Mg(py)$_2$].py (2.py). [Mg(Bu$''$)$_2$] (0.95 mL, 0.95 mmol), H$_2$-salo-Ph (0.30 g, 0.95 mmol) in toluene (~5 mL). Reaction turns red-orange in color; powder dries to a pale orange color. After stirring for 12 h, py addition yields a red product. Yield 84.2% (0.46 g). FTIR (KBr, cm$^{-1}$) 3053 (s), 2014 (s), 2955 (s), 2924 (s), 2869 (m), 1611 (s), 1583 (s, sh), 1546 (s), 1526 (s), 1483 (s, sh), 1469 (s), 1388 (s), 1302 (s), 1247 (w), 1220 (w), 1180 (s), 1147 (s), 1125 (m), 1107 (m), 1077 (w), 1041 (m), 1001 (m), 976 (w), 918 (m), 856 (w), 840 (w), 801 (w), 749 (s), 701 (m), 618 (w, sh), 605 (w), 635 (m). $^1$H NMR (500.1 MHz, py-d$_5$) δ 9.09 (1H, s(br), NC$_5$H$_5$), 8.70 (2H, s(br), —C(H)=N—, NC$_5$H$_5$), 7.80-7.79 (1H, mult., OC$_6$H$_5$), 7.54 (1H, t, J$_{H—H}$=7.6 Hz, OC$_6$H$_5$), 7.48 (1H, d, J$_{H—H}$=3.9 Hz, OC$_6$H$_5$), 7.33 (1H, t, J$_{H—H}$=7.6 Hz, NC$_5$H$_5$), 7.24-7.31 (1H, mult., $OC_6H_5$, $N-C_6H_5$), 7.21 (2H, t, $J_{H-H}$=7.4 Hz, $OC_6H_5$, $N-C_6H_5$), 6.55 (1H, t, $J_{H-H}$=7.4 Hz, $O-C_6H_5$). Elemental Analysis calc'd for $C_3H_{24}MgN_4O_2$ (2, MW=496.85): C, 72.52; H, 4.87; N, 11.28. Found: % C, 71.59; % H, 5.82; % N, 8.27.

[($\kappa^4$-(O,N,N',O')salo-Bu)Mg(py)$_2$] (3). [Mg(Bu$^n$)$_2$] (2.03 mL, 2.03 mmol), H$_2$-salo-Bu$^t$(1.00 g, 2.03 mmol) in toluene (~15 mL) and py (~1.5 mL). Reaction turns yellow in color; powder dries to a light brown. Yield 90.0% (1.23 g). FTIR (KBr, cm$^{-1}$): 2956 (s), 2868 (s), 1629 (s), 1545 (w, sh), 1528 (m), 1467 (s), 1441 (s), 1414 (m), 1391 (m), 1360 (m), 1336 (w), 1300 (w), 1275 (w), 1275 (w, sh), 1257 (m), 1233 (w), 1217 (w), 1200 (w), 1160 (m), 1089 (w), 1070 (w), 1037 (w), 986 (w), 909 (w), 878 (w), 852 (w, sh), 833 (w), 806 (w), 793 (w), 757 (w), 744 (w), 702 (m), 621 (w), 476 (w), 432 (w). $^1$H NMR (500.1 MHz, py-d$_5$) δ 8.70 (1H, d, $J_{H-H}$=2.1 Hz, NC$_5$H$_5$), 8.31 (1H, s, $-C(H)=N-$), 7.67 (1H, t, $J_{H-H}$=2.6 Hz, OC$_6$H$_2$Bu$^t_2$), 7.52 (0.5H, t, $J_{H-H}$=1.7 Hz, NC$_5$H$_5$), 7.29 (1H, d, $J_{H-H}$=2.6 Hz, OC$_6$H$_2$Bu$^t_2$), 7.17 (1H, t, $J_{H-H}$=1.7 Hz, NC$_5$H$_5$), 3.39 (2H, s, $-N-CH_2-$), 1.59 (9H, s, OC$_6$H$_2$(C(CH$_3$)$_3$)$_2$), 1.23 (9H, s, OC$_6$H$_2$(C(CH$_3$)$_3$)$_2$). Elemental Analysis calc'd for $C_{42}H_{56}MgN_4O_2$ (MW=673.24): C, 74.93; H, 8.38; N, 8.32. $C_{37}H_{51}MgN_3O_2$ (MW=594.14; 3-1 py): C, 74.80; H, 8.65; N, 7.07. Found: % C, 75.43; % H, 8.35; % N, 6.45.

[($\kappa^4$-(O,N,N',O')saloPh-Bu)Mg(py)$_2$].tol (4.tol). [Mg(Bu$^n$)$_2$] (1.85 mL, 1.85 mmol), H$_2$-saloPh-Bu$^t$ (1.00 g, 1.85 mmol) in toluene (~15 mL) with a py (~1.5 mL). Yield 93.7% (1.41 g). Reaction turns yellow in color; powder dries to a light brown. FTIR (cm$^{-1}$): 3071 (w); 2995 (w); 2951 (s); 2904 (m); 2864 (m); 1604 (s); 1578 (s); 1546 (s); 1464 (s); 1438 (s); 1387 (s); 1360 (s); 1248 (m); 1191 (m); 1159 (s); 1134 (s); 1109 (m); 1042 (m); 978 (m); 836 (m); 795 (s); 746 (s); 699 (s). $^1$H NMR (500.1 MHz, py-d$_5$) δ 9.25 (1H, s(br), NC$_5$H$_5$), 8.70 (2H, s(br), $-C(H)=N-$, NC$_5$H$_5$), 7.90-7.88 (1H, mult., OC$_6$H$_2$Bu$^t_2$), 7.68 (1H, t, $J_{H-H}$=7.3 Hz, OC$_6$H$_2$Bu$^t_2$), 7.45 (1H, t, $J_{H-H}$=7.6 Hz, NC$_5$H$_5$), 7.33-7.22 (1H, mult., OC$_6$H$_2$Bu$^t_2$, $N-C_6H_5$), 7.18 (2H, t, $J_{H-H}$=7.4 Hz, OC$_6$H$_2$Bu$^t_2$), 1.78 (9H, s, OC$_6$H$_2$(C(CH$_3$)$_3$)$_2$), 1.31 (9H, s, OC$_6$H$_2$(C(CH$_3$)$_3$)$_2$). Elemental Analysis calc'd for $C_{53}H_{64}MgN_4O_2$ (MW=813.43): C, 78.26; H, 7.93; N, 6.89. $C_{99}H_{120}Mg_2N_8O_4$ (MW=1534.71; 4+½ tol): C, 77.48; H, 7.88; N, 7.30. Found: % C, 77.03; % H, 8.62; % N, 6.55.

[($\kappa^3$-(O,N,N'),μ-(O')saloPh-Bu)Mg]$_2$ (5). [Mg(Bu$^n$)$_2$] (0.46 mL, 0.46 mmol), H$_2$-saloPh-Bu$^t$ (0.25 g, 0.46 mmol) in toluene (~15 mL). Yield 92.2% (0.24 g). Reaction turns dark brown in color; powder dries to orange. FTIR (cm$^{-1}$): 2956 (s), 2905 (s), 2867 (s), 1614 (s), 1581 (s), 1528 (s), 1463 (s), 1438 (m), 1409 (w), 1385 (m), 1360 (m), 1333 (w), 1259 (s), 1197 (m), 1167 (s), 1136 (w), 1108 (w), 1025 (w), 974 (w), 927 (w), 872 (w), 834 (w), 795 (w), 749 (m), 695 (w), 637 (w), 535 (w), 522 (w). Elemental Analysis calc'd for $C_{72}H_{92}Mg_2N_4O_4$ (5, MW=1126.16): C, 76.79; H, 8.23; N, 4.98. Found: % C, 76.60; % H, 8.31; % N, 4.64.

General Ca-salen reaction. In an inert atmosphere glovebox, a pre-weighed sample of the desired H$_2$-saloR'—R was added to a stirring solution of [Ca(NR$_2$)$_2$] in toluene. After stirring for 12 h, py was added and the reaction stirred for at least 1 h and then set aside with the cap removed until X-ray quality crystals grew.

[($\kappa^4$-(O,N,N',O')salo-Bu$^t$)Ca(py)$_3$] (6). [Ca(NR$_2$)$_2$] (0.732 g, 2.03 mmol), H$_2$-salo-Bu$^t$ (1.00 g, 2.03) in toluene (~15 mL) and py (~1.5 mL). The reaction turns pale yellow in color; powder dried to off-white powder. Yield 89.8% (1.40 g). FTIR (cm$^{-1}$): 3060 (w), 2956 (s), 2906 (s), 2867 (s); 1624 (s, C=N); 1525 (m); 1464 (s); 1438 (s); 1392 (m); 1359 (s); 1270 (s); 1252 (s); 1200 (m); 1154 (m); 1041 (s); 973 (s); 931 (s); 879 (s); 774 (s); 728 (s); 694 (s); 645 (m). $^1$H NMR (500.1 MHz, py-d$_5$) δ 8.70 (0.5H, d, $J_{H-H}$=2.7 Hz, NC$_5$H$_5$), 8.31 (1H, s, $-C(H)=N-$), 7.64 (1H, s(br), OC$_6$H$_2$Bu$^t_2$), 7.54 (0.5H, t, $J_{H-H}$=7.5 Hz NC$_5$H$_5$), 7.29 (1H, s(br), OC$_6$H$_2$Bu$^t_2$), 7.18 (0.5H, t, $J_{H-H}$=7.5 Hz, NC$_5$H$_5$), 3.30 (2H, s, $-N-CH_2-$), 1.37 (9H, s, OC$_6$H$_2$(C(CH$_3$)$_3$)$_2$), 1.33 (9H, s, OC$_6$H$_2$(C(CH$_3$)$_3$)$_2$). Elemental Analysis calc'd for $C_{47}H_{61}CaN_5O_2$ (6, MW=768.12): C, 73.49; H, 8.01; N, 9.12. Found: % C, 72.79; % H, 8.22; % N, 9.17.

[($\kappa^4$-(O,N,N',O')saloPh-Bu)Ca(py)$_3$].py (7.py). [Ca(NR$_2$)$_2$] (0.667 g, 1.85 mmol), H$_2$-saloPh-Bu$^t$ (1.00 g, 1.85 mmol) in toluene (~15 mL) and py (~1.5 mL). The reaction turns dark yellow in color; powder dried to yellow-orange powder. Yield 93.2% (1.27 g). FTIR (cm$^{-1}$): 3060 (w); 2992 (w); 2946 (m); 2904 (m); 2866 (m); 1594 (s, C=N); 1573 (s); 1518 (m); 1436 (s); 1381 (m); 1358 (m); 1236 (m); 1195 (s); 1149 (s); 1032 (m); 976 (m); 875 (m); 796 (s); 744 (s); 699 (s). $^1$H NMR (500.1 MHz, py-d$_5$) δ 8.70 (mult., NC$_5$H$_5$), 8.55 (2H, s, CH=N), 7.63 (2H, s, OC$_6$H$_2$Bu$^t_2$), 7.55 (2H, mult, NC$_5$H$_5$), 7.33 (2H, s, OC$_6$H$_2$Bu$^t_2$), 7.19 (mult. NC$_5$H$_5$), 7.05 (4H, s, C$_6$H$_4$), 1.51 (9H, s, OC$_6$H$_2$Bu$^t_2$), 1.37 (9H, s, OC$_6$H$_2$Bu$^t$2). Elemental Analysis calc'd for $C_{56}H_{66}CaN_6O_2$ (7.py, MW=895.26): C, 75.13; H, 7.43; N, 9.39. $C_{51}H_6CaN_5O_2$ (7.py, MW=737.06): C, 74.96; H, 7.66; N, 7.60. Found: % C, 75.52; % H, 8.10; % N, 7.34.

Proppant Loading. The pore volume of the proppant is reported to be 0.112 mL/g, and no more than 90% of pore volume was to be occupied by complex in solution during the impregnation process. Therefore, the precursor loading was between 2 and 6 wt. % using an infusion (or impregnation) process that is similar to that used in the preparation of heterogeneous catalysts. To a pre-weighed vial, the desired amount of metal salen complex was added to 10 mL of toluene (referred to as saloR-Bu$^t$ solution). The proppant was weighed (10.0 g) into a separate vial and 0.8 mL of saloR-Bu$^t$ solution was added dropwise to the vial containing proppant and adsorbed into the pores. After each addition, the vial was shaken, and the excess toluene removed in vacuo. This process was repeated until the desired wt. % loading was achieved. Loadings: Compound 3 (0.479 g) loading achieved 4.79 wt. % of 3 in proppant, Compound 4 (0.632 g) loading achieved 6.32 wt. % of 4 in proppant, and compound 7 (0.648 g) loading achieved 6.48 wt. % of 7 in proppant.

Elution studies: Laboratory experiments designed to mimic fluid flow through hydraulically-fractured zones in a subsurface well that contain a ceramic proppant were conducted. In general, the experimental setup uses a cartridge pump to send the desired solvent fluid (either aqueous or hydrocarbon) at a constant rate through a small "proppant pack" to a fraction collector. The proppant pack consists of porous proppants that have been infused with the metal salen compounds which are packed into a plastic syringe equipped with a fine mesh proppant retention screen at the entrance tip. The pore volume—a measure of the fluid volume within the pack of proppant pellets—is measured. The proppant pack is then sealed at the top with a rubber septum to generate pressure to force the exiting fluid into tubing for transport to the collection test tubes in the fraction collector. Samples were collected over many pore volumes and the concentrations of metal complexes in the samples were measured by either Atomic Absorption Spectrophotometry (AAS) or Raman spectroscopy after the desired number of pore volumes had passed over the proppant pack. Side by side experiments using coated proppant packages versus identical proppant packages without the coating demonstrated conclusively that the presence of the coating material significantly slowed the release of the tracer material into the solvent fluid during the early stages of use. This retardation of tracer release in the early stage of use is important as it will extend the useful life of the tracer in practical applications, as the total amount of tracer that can be loaded is limited by the porosity of the proppant and solubility of the M-L metal complex.

Results and Discussion.

A search of the structure literature reveals that surprisingly few alkaline earth salen derivatives have been reported. Of the 22 compounds structurally characterized with at least one alkaline earth metal coupled to a salen backbone, the majority of the family members are heterometallic species with the alkaline earth cations located externally to the salen-cavity, including: Mg—Cu, Mg—Ni, Ca—Ni, Ca—U, Ca—Cu, Sr—Cu, Ba—Cu, Ba—Ni, and Ba-Fe. Only six homo-metallic compounds have been reported: [Be(μ-($\kappa^4$-(O,N,N',O')salen))]$_2$.H$_2$O, bis(μ-3,3'-(ethane-1,2-diyl bis(iminiomethyl ylidene)) bis(2-oxybenzoate))di-aqua, di-magnesium hexahydrate), aqua,methanol-(ethylendiamine-N,N'-bis(2-aldimino-4-methyl-6-formylphenolato)) magnesium, (THF)(HOEt)$_2$Ca($\kappa^4$-(O,N,N'O')salo-Bu, (DME)Ca($\kappa^4$-(O,N,N'O')saloCy-Bu), where saloCy-Bu$^t$=bis(3,5-di-t-butylsalicylidene)cyclohexane-1,2-diamine, (HOEt)$_3$Sr($\kappa^4$-(O,N,N'O')salo-Bu$^t$). It is of note that [Mg(salen)]$_2$ and [Mg(salo-Ph)]$_2$ were reported from the reaction of [Mg(CH$_2$C$_6$H$_5$)$_2$] and the respective Schiff-base; however, these products were not crystallographically characterized.

Mg Complexes.

The reaction of [Mg(Bu$^n$)$_2$] with the commercially available H$_2$-salen or H$_2$-saloPh was undertaken in toluene (eq 1). For the H$_2$-salo ligand, the products formed were found to be insoluble in toluene but upon addition of the strong Lewis base py, clear, orange solutions could be obtained at elevated temperatures. All attempts to generate single crystals yielded only amorphous powders. Switching to the H$_2$-saloPh ligand led to a clear, dark-orange solution in warm toluene. The crystals that grew upon slow cooling were identified as compound 1. Initial inspection of the structure of 1 reveals four Mg(saloPh) moieties that are interconnected through the oxygen atoms from the phenoxide rings: two terminal (one bridges) and two internal (both bridge). This results in a chain of [(μ-O)-Mg]$_4$ with two trigonal bipyramidal ($\tau$=0.37) and two pseudo-octahedral (OC-6) bound Mg metal centers. Upon closer examination of the second saloPh ligand, surprisingly, an n-butyl group was solved, branching off the carbon of the 'Ph-C(34)=N(4)-Mg(2)' moiety. This indicates that a C—C bond was formed in this simple reaction. This mechanism is not fully understood but the use of the basic [Mg(Bu$^n$)$_2$] may lead to de-protonation of the Ph-C(H)=N fragment. Isolation of crystals from this reaction have not been easily reproducible and the structure suffers from weak diffraction.

Alternatively, the product isolated from the Lewis basic solvent py was found to be the mononuclear compound 2 (FIG. 3). Compound 2 is the first report of a structurally characterized, alkaline earth salen derivative with a bound py solvent molecule. The coordination of the Mg is best described as pseudo octahedral (OC-6) using the full complement of available binding sites on the saloPh-Bu$^t$($\kappa^4$-O,N,N',O') ligand along with two trans bound py solvent molecules.

Salen derivatives with t-butyl groups on the rings were of interest due to their expected increased solubility in organic solvents. Both the ethyl and phenylene diamine derivatives were synthesized following literature routes, wherein 3,5-di-tert-butyl-2-hydroxybenzaldehyde was condensed with ethylene-1,2-diamine or o-phenylene-1,2-diamine forming N,N'-bis(3,5-di-t-butylsalicylidene)-ethylenediamine (H$_2$-salo-Bu$^t$, FIG. 1c) or N,N'-bis(3,5-di-t-butylsalicylidene)-1,2-phenylenediamine (H$_2$-saloPh-Bu$^t$), respectively. Once isolated and characterized, these ligands were reacted with [Mg(Bu$^n$)$_2$], following eq 1. The products isolated were identified by single crystal X-ray diffraction studies as the monomeric species 3 and 4. The saloR-Bu$^t$ derivatives act in the same tetradentate manner binding through the $\kappa^4$-O,N,N',O' atoms with trans axial py molecules.

Attempts to reproduce an improved crystal of 4 led to the isolation of 4a. While the binding mode of the salo-Bu$^t$ to the Mg for both compounds are identical, only one py solvent molecule was solved bound to the Mg cation of 4a. This limited solvation places the Mg in a 5-coordinate square base pyramidal ($\tau$=0) geometry. A rational route to the mono- (4a) versus the di-substituted (4) has not been discerned, as of yet. Since the ability to bind a variable number of solvent molecules is unexpected and difficult to control, the structure parameters were reported to allow for ease of identification. There are some differences in the metrical data of 4 and 4a. In particular, the Mg-N distance of the di-substituted species is over 0.15 Å longer. This weaker interaction is also reflected in the 6° and 10° larger bond angles of O-M-O and O-M-N, respectively. Based on these metrical data, the number or type of solvent bound to the metal may play a bigger role in the final stability of these compounds in real-world efforts, than originally anticipated.

It was of interest to determine if the solventless structures for the saloPh-Bu$^t$-Mg derivatives could be obtained and what their structural arrangement would be. Following the same reaction pathway noted above but omitting the addition of py led to the crystallization of compound 5. This compound was characterized by single crystal X-ray diffraction as a dinuclear complex. For 5, each 5-coordinated Mg was solved in a square base pyramidal geometry ($\tau$=0.96) binding in a $\kappa^3$-(O,N,N'),μ-(O') chelation mode, where the second O atom from each saloPh-Bu bridges two Mg centers.

Ca Complexes.

As the Ca(R)$_2$ precursors are not readily available, derivatization of H$_2$-salen or H$_2$-saloPh were investigated using [Ca(NR$_2$)$_2$] in toluene (eq 2). For both reactions, the parent metal-salen complex product rapidly precipitated upon mixing and remains insoluble in hot toluene. The salo-But and saloPh-Bu$^t$ products were soluble in py and upon crystallization by slow evaporation yielded the monomeric py-containing derivatives 6 and 7. A CN-7 geometry around the metal occurs from the tetradentate salo-ligand ($\kappa^4$-O,N,N', O') and the coordination of 3 py solvent molecules. The phenyl rings of the salo-Bu$^t$ are planar but at the cost of a twisted ethyl group on the diamine (27.9°). In contrast, the rigidity induced by the phenyl ring of the saloPh-Bu$^t$ causes a substantial bend in the rings of the salo moiety.

Fluid Flow Parameters.

Critical for practical use, these salen-based tracers must survive at temperatures (up to about 150° C.) and pressures typically noted for deep-well conditions, easily loaded into, and freely elute from, the carrier proppants, remain soluble in the product fluids and flow to the surface without binding to underground strata so as not to alter both qualitative and quantitative results.

(iii) Elution data. As mentioned previously, in order for the prepared metal-salen ligand complexes to be useful in tracking fluid flows the infused complexes must elute from the underground proppants upon exposure to the produced fluid, and remain soluble until they are analyzed aboveground. As the fluid flowing from underground is typically a mixture of hydrocarbons (i.e., organic product) and water, when eluted they will partition into either the organic or aqueous phases. Laboratory-scaled elution testing equipment was used to simulate the "real world" performances of experimental samples by flowing the desired fluid over a proppant pack and measuring the amount of complex found in sample aliquots over time. There are at least three key points to keep in mind when evaluating these samples.

First, the amount of complex released into the produced fluid is expected to decrease over time as the concentration of infused complex decreases within the proppant. Elution experiments were conducted at a constant flow rate and aliquots taken as a function of time. The eluted fluid volume is converted to pore volumes for elution profile analysis.

Second, the testing solvent can be either an aqueous salt solution that simulates a formation brine or a long-chain hydrocarbon (such as Isopar L) to mimic the organic products. Typically, it is much easier to analyze samples in aqueous media as inductively coupled plasma techniques can be used to accurately measure the metal concentration. However, for this effort, evaluating the Mg-salen concentrations in hydrocarbons was of interest. As such, a procedure using AAS was developed to analyze the low Mg levels found in the organic solvent. The amount of eluted tracer could also be measured using quantitative Raman spectroscopy.

Third, it is possible to put a polymeric coating on proppant particles to retard the elution rate of the Mg-salen species from the package and thus extend the operating lifetime of the proppant package. However, the goal was to experimentally demonstrate the concept that the M-salen (M=Mg, Ca) complexes developed could function as taggants for monitoring underground fluid flow.

For this report, our initial analyses were undertaken on a proppant pack infused with 4. As expected, the level of eluted Mg-salen complex decreased markedly from the initial phase of the testing (176 ppb, aliquot taken after four pore volumes had been collected) to the intermediate sampling taken at the 20 pore volume mark (29 ppb), to the latter stages of testing at the ~40 pore volume mark (9 ppb). This decline was shown, and these results indicate that these salen-metal species loaded into proppants meet our preliminary requirement that they gradually elute from the proppant package over time.

CONCLUSION AND SUMMARY

The Ca and Mg saloR'—R species were found to possess the proper stability and solubility under deep well mimicked conditions. Proppant packages containing soluble Mg-salen and Ca-salen tracer complexes have been shown to gradually release the tracer material into hydrocarbon or aqueous environments and continue to elute the tracers over an extended period of time.

The present invention is further directed to methods for monitoring underground fluid flows that include providing a proppant that includes a tracer that is a soluble chelating ligand including a metal. In an embodiment, the tracer may be released at a known rate, allowing for a determination of fluid flow characteristics. The soluble chelating ligands do not adsorb in the formation and have distinct spectroscopic properties that aid analysis and rate determinations.

According to an embodiment of the disclosure, the tracer disclosed above is introduced into a subterranean formation and thereafter collected at locations distant from the introduction site. For example, a tracer may be introduced at a well bore and collected at other well bores. In such a manner, the fluid flow connectivity and rate of flow between various well bores can be determined.

According to another embodiment of the disclosure, a proppant containing the tracer above may be introduced into a subterranean formation and the tracer thereafter collected at locations distant from the introduction site. For example, a proppant containing tracer may be introduced at a well bore and the tracer may be collected at other well bores. In such a manner, the fluid flow connectivity and rate of flow between various well bores can be determined.

The present disclosure is further directed to methods of diagnostic evaluation of a hydraulic fracturing stimulation of a Subterranean formation, including: injecting a hydraulic fluid into at least one stage of the subterranean formation at a rate and pressure sufficient to open a fracture therein, the Subterranean formation including one or more formation fluids and the hydraulic fluid including a proppant composition including a plurality of particulates, at least one of particulate of the plurality of particulates containing at least one tracer; wherein the at least one tracer separates from the proppant composition continuously over a period of time; wherein the at least one tracer returns to the surface with the formation fluids; and wherein the at least one tracer is recovered and identified.

In addition to determining which stages of a hydraulically fractured well are producing hydrocarbons and/or water it may be desirable to determine the fraction of the created fracture that is contributing to the flow of fluids. Estimates of the length and heights of the created fracture are possible by various means well known to those of ordinary skill in the art. According to several exemplary embodiments, methods using a tracer to determine differing subterranean characterizations as disclosed in U.S. Patent Publication Number 2016/0075937, are hereby incorporated by reference in its entirety.

According to an embodiment, the tracer separates from the tracer containing proppant after the tracer containing proppant is injected into the fracture. In several exemplary embodiments, separation of the tracer from the tracer containing proppant can be accomplished by the tracer leaching, eluting, diffusing, bleeding, discharging, draining, seeping, or leaking out of the porous proppant and/or the coated proppant, or any combination thereof. Further, this leaching, eluting, diffusing, bleeding, discharging, draining, seeping, or leaking out of the porous proppant and/or the coated proppant, or any combination thereof can be further controlled by a permeable, semi-permeable, and/or degradable coating. According to several exemplary embodiments, the porous ceramic proppant infused with a tracer are coated with a polymeric material that forms a semi-permeable polymeric coating that is substantially non-degradable in the presence of the well fluids but permits the tracer to leach, elute, diffuse, bleed, discharge, desorb, dissolve, drain, seep, and leak through the polymeric coating so as to release the tracer into the fracture or well area.

According to several exemplary embodiments, the coated, tracer containing proppant is coated with a polymeric material that forms a semi-permeable polymeric coating that is substantially non-degradable in the presence of the well fluids but permits the tracer to leach, elute, diffuse, bleed, discharge, desorb, dissolve, drain, seep, and leak through the polymeric coating so as to release the tracer into the fracture or well area. According to an embodiment, a proppant composition may include both organic and aqueous soluble tracers to determine separation of fluid flow types within the formation. In an embodiment, the release of the tracer may be as disclosed in U.S. Patent Publication Number 2016/0075937, hereby incorporated by reference in its entirety.

The invention being thus described, it will be obvious that the same may be varied in many ways. Such variations are not to be regarded as a departure from the spirit and scope of the invention, and all such modifications as would be obvious to one skilled in the art are intended to be included within the scope of the appended claims. It is intended that the scope of the invention be defined by the claims appended hereto. The entire disclosures of all references, applications, patents and publications cited above are hereby incorporated by reference.

In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method, comprising:
   introducing a modified proppant into a subterranean formation, wherein the modified proppant comprises a proppant and a metal ligand complex in contact with the proppant; and
   collecting a fluid comprising the metal ligand complex from the subterranean formation;
   wherein the metal ligand complex comprises:
   a salen or salen derivative ligand.

2. The method of claim 1, further comprising:
   analyzing the fluid for an amount of the metal ligand complex by a method selected from a group consisting of Fourier Transformed InfraRed, Raman, and resonance Raman spectroscopy.

3. The method of claim 1, wherein the modified proppant is introduced by injecting the modified proppant into a well bore.

4. The method of claim 1, wherein the modified proppant is collected at a well bore.

5. The method of claim 1, wherein the proppant is porous.

6. The method of claim 1, wherein a polymer or resin is in contact with the particulate or metal ligand complex.

7. The method of claim 1, wherein the metal ligand complex comprises a ligand or ligand derivative selected from a group consisting of porphyrins, phthalocyanines or salens and their modified derivatives.

8. The method of claim 1, wherein the proppant is a porous ceramic particulate.

* * * * *